United States Patent [19]
Trott et al.

[11] Patent Number: 5,803,733
[45] Date of Patent: Sep. 8, 1998

[54] PNEUMATIC SURGICAL HANDPIECE AND METHOD

[75] Inventors: A. Frank Trott, Largo; W. Lane Ector, Jr., Seminole, both of Fla.

[73] Assignee: Linvatec Corporation, Largo, Fla.

[21] Appl. No.: 851,902

[22] Filed: May 6, 1997

[51] Int. Cl.⁶ .................................................. A61C 1/05
[52] U.S. Cl. .......................................... 433/132; 415/904
[58] Field of Search .............................. 433/132; 415/904

[56] References Cited

U.S. PATENT DOCUMENTS

| | | | |
|---|---|---|---|
| 1,061,142 | 5/1913 | Tesla | 415/90 |
| 1,061,206 | 5/1913 | Tesla | 415/90 |
| 1,183,075 | 5/1916 | Kiefer | 415/218.1 |
| 2,020,793 | 11/1935 | Meininghaus | 415/84 |
| 2,099,699 | 11/1937 | Meininghaus | 415/84 |
| 2,173,786 | 9/1939 | Lowis | 415/188 |
| 2,251,057 | 7/1941 | Iseman | 433/106 |
| 2,471,653 | 5/1949 | Price | 415/188 |
| 2,606,502 | 8/1952 | Carlson | 415/83 |
| 3,046,585 | 7/1962 | Ledingham et al. | 415/904 |
| 3,052,984 | 9/1962 | Mitthauer et al. | 433/100 |
| 3,076,266 | 2/1963 | Johansson | 433/100 |
| 3,107,625 | 10/1963 | Amberg | 415/226 |
| 3,128,988 | 4/1964 | Mandroian | 433/132 |
| 3,141,650 | 7/1964 | Saffir | 433/132 |
| 3,203,514 | 8/1965 | Davies et al. | 188/170 |
| 3,205,828 | 9/1965 | Rupp | 415/199.1 |
| 3,270,678 | 9/1966 | La Monica | 415/206 |
| 3,468,385 | 9/1969 | Penza | 415/904 |
| 3,469,318 | 9/1969 | Saffir | 433/132 |
| 3,627,280 | 12/1971 | Fridman et al. | 415/199.2 |
| 3,695,367 | 10/1972 | Catterfeld et al. | 173/221 |
| 3,709,630 | 1/1973 | Pohl et al. | 415/199.5 |
| 3,733,143 | 5/1973 | Theis, Jr. | 433/132 |
| 3,761,195 | 9/1973 | Eskeli | 415/1 |
| 3,779,667 | 12/1973 | Johnson | 415/172.1 |
| 3,867,655 | 2/1975 | Stengel et al. | 310/66 |
| 4,011,027 | 3/1977 | Selder | 415/121.3 |
| 4,060,336 | 11/1977 | Theis, Jr. et al. | 415/80 |
| 4,087,198 | 5/1978 | Theis, Jr. | 415/82 |
| 4,361,414 | 11/1982 | Nemes et al. | 415/83 |
| 4,874,575 | 10/1989 | Dunn et al. | 376/404 |
| 5,074,750 | 12/1991 | Kakimoto | 415/200 |
| 5,137,424 | 8/1992 | Daniel | 415/206 |
| 5,211,531 | 5/1993 | Kakimoto | 415/112 |
| 5,304,033 | 4/1994 | Tang | 415/206 |
| 5,427,499 | 6/1995 | Kirby | 415/90 |
| 5,439,346 | 8/1995 | Bowser et al. | 415/18 |

*Primary Examiner*—John J. Wilson
*Attorney, Agent, or Firm*—Gene Warzecha

[57] ABSTRACT

A pneumatically powered surgical handpiece suitable for a pencil-type handpiece configuration in which the pressurized fluid inlet is axially directed relative to the handpiece body. Fluid is directed through a dispersing section from an axial direction to a radially outward direction against the interior of a hollow cylindrical turbine body provided with a plurality of circumferentially arranged and longitudinally extending semi-circular channels adapted to receive the fluid flow and redirect it proximally through an annular exhaust channel situated annularly about the fluid inflow conduit. An output shaft is integrally formed with the turbine body and extending distally therefrom and a surgical instrument may be attached to or integrally formed within this output shaft. The invention also resides in a method for fluidically driving a surgical handpiece and lends itself to a method of producing a disposable fluidically driven surgical instrument.

22 Claims, 9 Drawing Sheets

PNEUMATIC SURGICAL HANDPIECE AND METHOD

BACKGROUND OF THE INVENTION

1. Field of the Invention

This invention relates to a pneumatic surgical handpiece. More particularly, this invention relates to a turbine driven, pencil-type pneumatic surgical handpiece having a fluid inlet at one end for driving an axially aligned surgical instrument at the opposite end.

2. Description of the Prior Art

Pneumatic surgical handpieces generally rely on compressed fluid flow through a bladed or finned impeller turbine rotor situated in the handpiece housing and are commonly used in various surgical and dental procedures. Bucket-type rotors are also known although they are generally inefficient in converting the energy of the fluid into rotor torque because only one bucket is operative at any one time. While these devices are available in diameters as small as one-half inch (12.5 mm) or so and lengths as short as three inches (75 mm) or so, the speeds and torques produced by these devices are highly dependent on the size of the components and the operating pressure. The present invention is directed to the goal of maximizing the speeds and torques available within a given size handpiece while retaining other characteristics desirable in surgical handpieces (i.e. acceptable noise and heat levels, etc.). It is always beneficial to maximize power output of these handpieces relative to their size thereby providing the user with increased flexibility to use the devices in varying new surgical procedures, especially those in tight work spaces such as ear-nose-throat (ENT) procedures.

While the preferred embodiment of the invention is described in the context of a pneumatic, air or gas driven device, it will be understood that other fluids may be equally applicable. The term "fluidic" may be used interchangeably to refer to any gas or liquid.

A multi-stage axial type turbine rotor for a dental handpiece is shown in U.S. Pat. No. 3,469,318 (Saffir). This device shows a cylindrical rotor barrel having a plurality of turbine blades extending radially outwardly from the barrel in a plurality of longitudinally spaced, circularly parallel rows. This device directs air inflow and exhaust in conduits aligned with the handpiece axis and rotates an output shaft (supported by bearings at each end) which in turn rotates the drill (or other instrument) about an axis generally transverse to the handpiece axis.

A pencil-type handpiece in which the instrument is rotated about an axis in line with the handpiece is shown in U.S. Pat. No. 5,074,750 (Kakimoto) in which an axially aligned fluid inlet conduit provides pressurized fluid for impinging radially inwardly on a cylindrical rotor body attached to the output shaft of the handpiece. The exhaust air is channeled proximally, away from the rotor body and through an annular exhaust channel surrounding the axially aligned fluid inlet conduit. The rotor is supported by bearings at each end of the turbine body.

Another prior art dental handpiece is shown in U.S. Pat. No. 5,211,531 (Kakimoto) in which a pencil-type handpiece is also provided with an axially aligned fluid inlet conduit and an annular exhaust channel concentric thereto. The fluid inlet is channeled radially inwardly toward a solid rotor provided with a plurality of longitudinally extending vanes for converting the forces within the pressurized fluid to rotation of the rotor (supported between two bearings).

While the preceding prior art embodiments utilize solid rotors with vanes and with fluid inlet flow directed axially through the vanes or radially inwardly (or tangentially) onto the rotors, some prior art embodiments are known which utilize hollow turbine rotors which receive pressurized fluid from within the rotor and direct it radially outwardly. For example, U.S. Pat. No. 3,141,650 (Saffir) shows a dental handpiece having a transversely situated turbine rotor in which pressurized fluid is directed axially into a hollow rotor supported between two bearings and provided with a plurality of apertures in its circumferential wall. The exhaust fluid is then directed radially outwardly from the rotor body.

All of these known devices have structures which limit the effective turbine rotor diameter and, therefore, the size of the handpiece for any given power output. It is believed that for a given outside diameter of the handpiece and fluid pressure the power available from a surgical handpiece may be maximized by the present invention. That is, speeds and torques comparable to prior art handpieces may be produced by a relatively narrower and shorter handpiece incorporating the principles of this invention. In pencil-type handpieces having axially aligned drill bits, for example, the turbine and/or its output shaft are supported by bearings at each end, thus adding to the length of prior art devices. Also, since bearings generate some frictional heat, all such devices are heated to some extent by the bearings. The subject invention utilizes a cantilevered turbine rotor supported by bearings on one side of the turbine body, thus enabling not only shorter devices but ones which may be expected to produce less heat.

Additionally, pneumatic handpieces should have some braking means to prevent operation of the device as pressure is turned off. That is, when a user wants a pneumatic drill to stop, it should do so quickly. While pneumatic braking mechanisms are known in general, none are known to have been applied to a surgical pneumatic handpiece.

It is, therefore, an object of this invention to produce a pencil-type pneumatic surgical handpiece which is able to maximize output speed and torque as compared to a prior art pneumatic surgical handpiece of the same outside diameter and length.

It is also an object of this invention to produce a turbine type pneumatic surgical handpiece which maximizes the amount of torque available within a given turbine diameter.

It is also an object of this invention to produce a turbine type pneumatic surgical handpiece having a rotor with a diameter maximized for a given handpiece diameter.

It is also an object of this invention to produce a turbine type pneumatic surgical handpiece, the length of which is minimized to provide greater control and access in tight work spaces.

It is another object of this invention to produce a turbine type pneumatic surgical handpiece which maximizes the speed and torque produced by the turbine for a given fluid input pressure.

It is an additional object of this invention to produce a shorter and cooler-running turbine type pneumatic surgical handpiece than is available in the prior art through the use of a cantilevered rotor, supported by bearings only on one side of the rotor.

It is yet another object of this invention to produce a pencil-type pneumatic surgical handpiece having a braking means for limiting operation of the device below a certain pressure level.

SUMMARY OF THE INVENTION

These and other objects of the invention are achieved by the preferred embodiment disclosed herein which is a pneumatic surgical handpiece for driving a surgical instrument comprising a tubular housing having proximal and distal ends. The tubular housing has an axis and retains a rotor means for converting forces within a pressurized fluid to motion of the surgical instrument. The rotor means is rotatably secured to the housing and comprises an axially aligned turbine body and an axially aligned output shaft extending distally from the turbine body. The turbine body comprises a distal end wall adjacent the output shaft, an open proximal end and an imperforate, axially aligned cylindrical wall extending proximally in cantilevered fashion from the distal end wall toward the open proximal end. The imperforate cylindrical wall surrounds an interior chamber bounded circumferentially by the interior surface of the cylindrical wall. A fluid inflow conduit means is attached to the tubular housing for communicating pressurized fluid to the interior surface of the turbine body to rotate the rotor about its axis. Means are provided for securing a surgical instrument to the output shaft.

The invention also resides in the method of fluidically driving a surgical instrument within a handpiece comprising the steps of providing a tubular housing having proximal and distal ends and an axis. A rotor means is then provided within the housing, the rotor means comprising an axially aligned turbine body and an axially aligned output shaft extending distally from the turbine body. The turbine body comprises a distal end wall adjacent the output shaft, an open proximal end and an imperforate, axially aligned cylindrical wall extending proximally from the distal end wall toward the open proximal end. The imperforate cylindrical wall surrounds an interior chamber bounded circumferentially by the interior surface of the cylindrical wall. A surgical instrument is secured to the output shaft and pressurized fluid is directed transversely to the interior surface of the turbine body, at a predetermined angle, to rotate the rotor about the axis. The method may further comprise rotatably supporting the rotor means in a cantilevered manner and directing the pressurized fluid axially in a distal direction prior to directing it transversely. Furthermore, the exhaust fluid may be directed proximally and through a coaxial dual lumen inlet/exhaust hose. The invention lends itself to producing disposable fluidically driven surgical instruments because of the simplicity of design and the small number of parts required for a fully functional unit. The surgical instruments may be burrs, drills, rotatable shavers, etc.

DESCRIPTION OF THE PREFERRED EMBODIMENT

Figure 1:
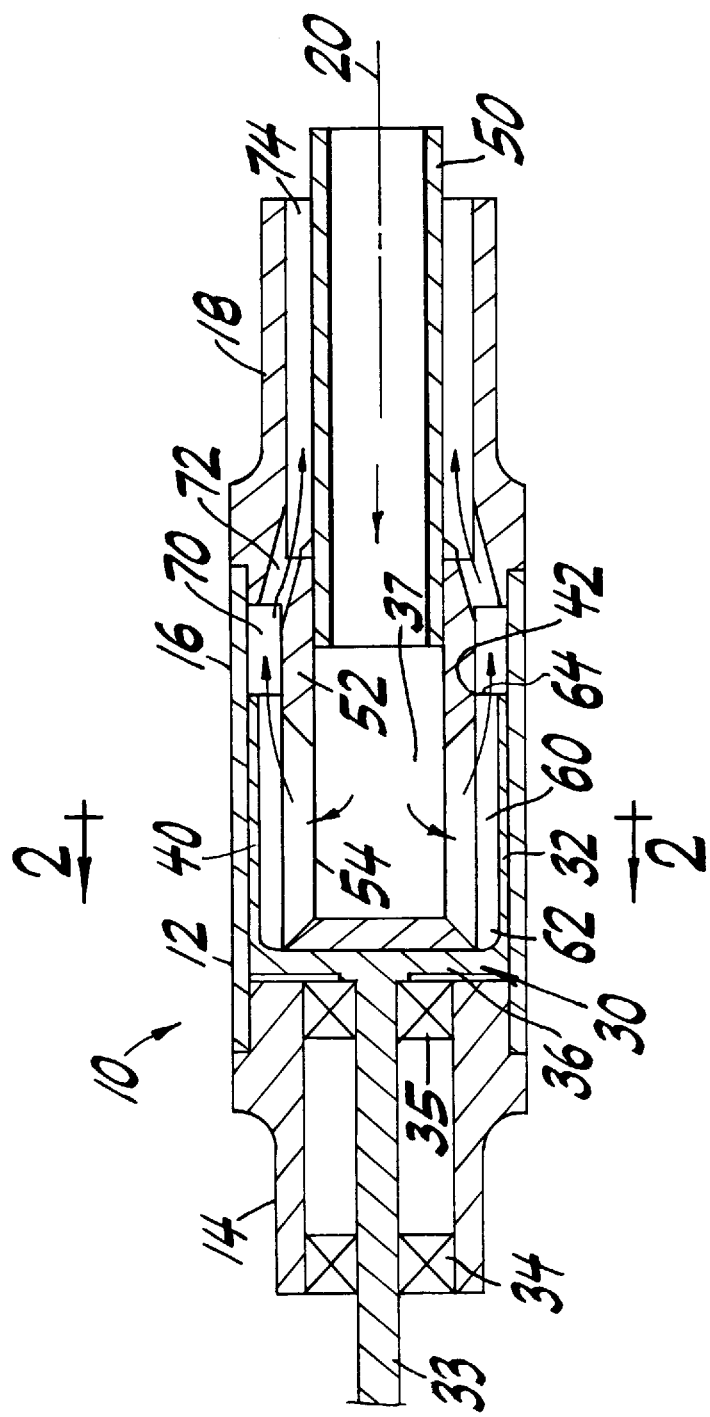
FIG. 1 is a schematic side elevational view in cross-section of a surgical handpiece constructed in accordance with the principles of this invention.

As shown in the drawings, surgical handpiece 10 is a pencil-type handpiece comprising a tubular housing 12 having a distal portion 14, a central portion 16 and a proximal portion 18 all aligned along a common axis 20. Rotatably received within housing 12 is a rotor assembly 30 comprising an open ended, turbine body 32 and an output shaft 33 extending distally from the turbine body. Bearings 34 and 35 support output shaft 33 so that the turbine body 32 may extend proximally from the shaft in a cantilevered manner. A drill bit or the like (not shown) may be attached to or integrally formed with the output shaft. The proximal portion 18 is connected to a dual lumen hose (not shown) for supplying to the handpiece a pressurized fluid and for conveying from the handpiece the exhaust fluid. It will be understood that other handpiece configurations may be adapted to utilize the principles of the invention disclosed herein. For example, as shown below in FIG. 5, a pistol-grip type of handpiece may incorporate the various elements with suitable gearing to increase, decrease or redirect the operation of the output shaft.

Turbine body 32 has a distally situated, transverse end wall 36 and an imperforate cylindrical wall 40 extending proximally from end wall 36. A rim 42 is situated at the proximal end of the turbine body and the interior of the rim adjacent axis 24 is open. Cylindrical wall 40 thus encloses an interior chamber 37 bounded by the cylindrical wall and end wall 36. The preferred embodiment enables the turbine body diameter to be maximized within housing portion 16 because very little clearance is necessary between the two components.

Figure 2:
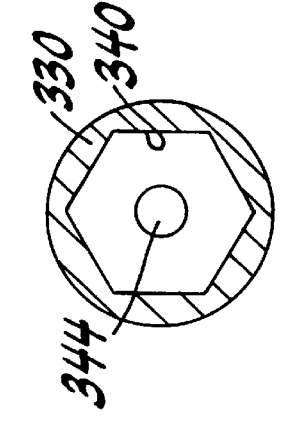
FIG. 2 is a view of FIG. 1 taken along the line 2—2.
Figure 7:
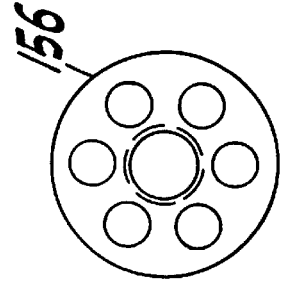
FIG. 7 is a sectional view of FIG. 6 taken along the line 7—7.
Figure 6:
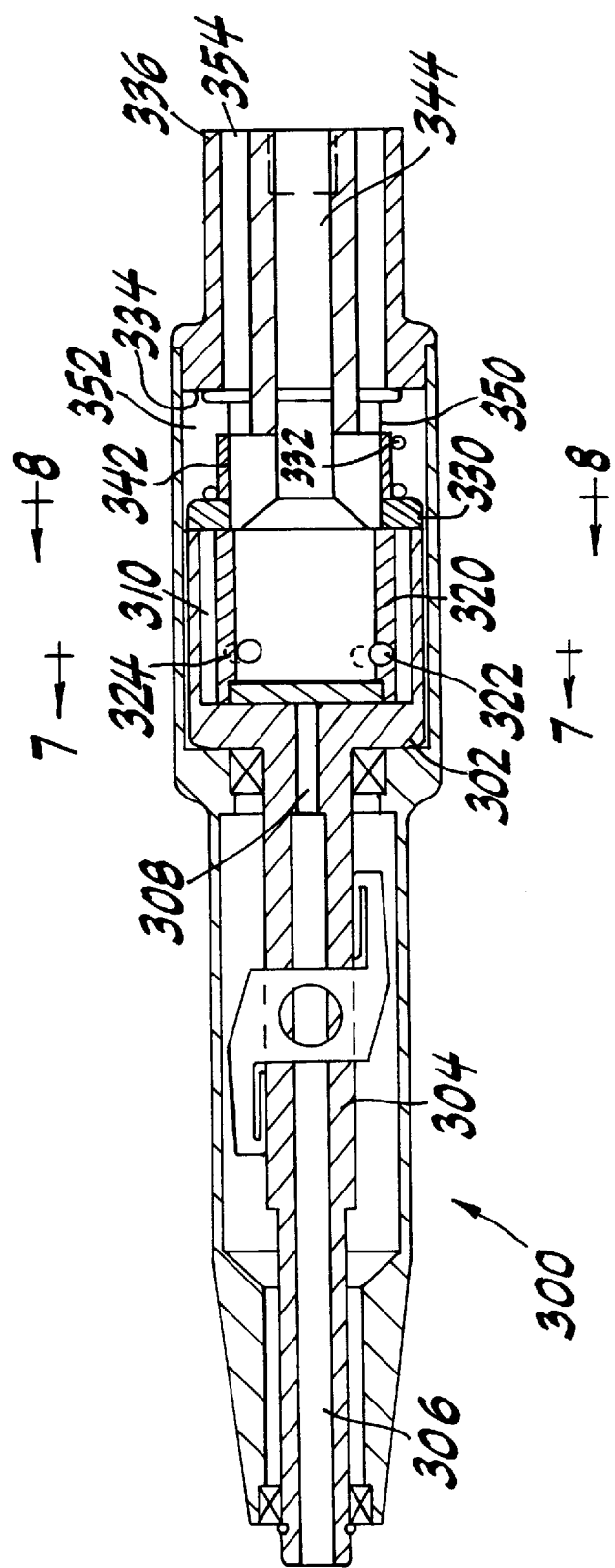
FIG. 6 is a schematic side elevational view in cross-section of another embodiment of a surgical handpiece constructed in accordance with the principles of this invention.

The proximal portion 18 of the tubular housing 12 receives axially aligned fluid inflow conduit 50 in order to direct pressurized fluid from a pressure source (not shown) to the interior chamber 37 of turbine body 32. In the preferred embodiment, the distal end of conduit 50 is provided with an axially aligned stationary dispersing cap 52 adapted to fit closely within the interior chamber 37 and to divert the fluid flow from an axial direction to a transverse, tangential direction toward the interior surface of the cylindrical wall 40. Dispersion cap 52 is provided with a plurality of circumferentially arranged ports in the form of longitudinally extending and obliquely oriented slots 54, as best seen in FIG. 2. The slots are adapted to not only divert the fluid flow transversely but by being inclined at a predetermined angle A relative to a radial line of the turbine body, the slots impart a tangential element to the flow direction. While six ports are shown here, it will be understood that the number, shape and arrangement of ports may be varied and, as shown in FIGS. 6 and 7, an embodiment with two diametrically opposed ports may be used. The overlapping design of turbine body 32 and deflector cap 52, facilitated by the cantilevered structure of the turbine body, enables the overall length of the handpiece to be minimized.

The interior surface of the turbine body is provided with a plurality of longitudinally extending arcuate surfaces in the form of channels 60, each of which has a closed distal end 62 adjacent end wall 36 and an open proximal end 64 adjacent rim 42. Depending upon the length of turbine body 32, an optional bearing means may be used to support rim 42, although this was not deemed necessary in the preferred embodiment in view of the materials, pressures and structures used. Actually, the open ends of the channels 60 coincide with open end 42 of the turbine body and open up into an annular chamber 70 from which exhaust air is directed through a plurality of annularly arranged channels 72 into an annular exhaust channel 74 concentrically situated about fluid inflow conduit 50.

Figure 4:
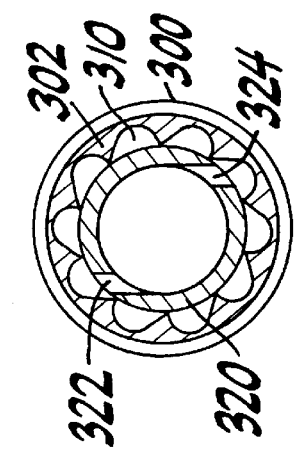
FIG. 4 is a right side view of FIG. 3.
Figure 3:
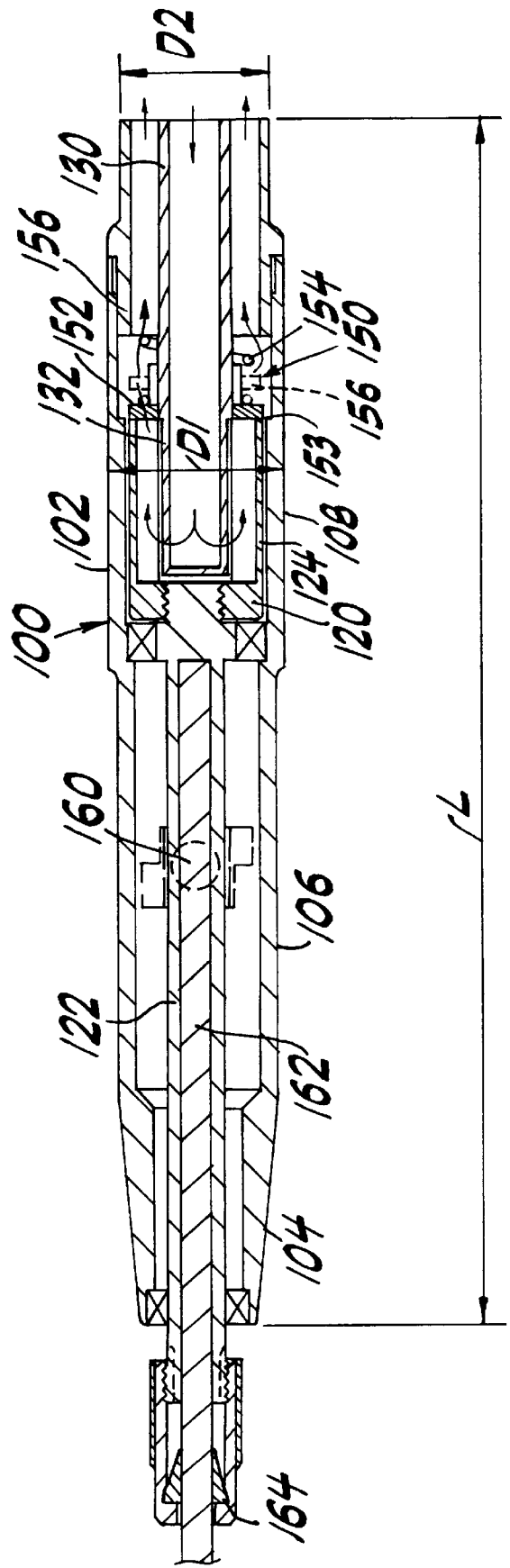
FIG. 3 is a side elevational view in cross-section of a preferred embodiment of this invention.

Referring now to FIGS. 3 and 4, a preferred embodiment of the invention incorporates the principles disclosed above with respect to FIGS. 1 and 2 and incorporates further improvements. Thus, surgical handpiece 100 comprises a housing body 102 integrally formed by a distal section 104, a central section 106 and a proximal section 108. Rotor 120, comprising hollow output shaft 122 and turbine body 124, is analogous to the comparable component in the embodiment of FIGS. 1 and 2. Axially aligned fluid inflow conduit 130 and distal dispersing cap 132 are also similar to comparable components in the previous embodiment. Handpiece 100 is provided with a pneumatic braking mechanism 150 in order to stop the rotation of rotor 120 below a predetermined fluid pressure within conduit 130. Braking mechanism 150 comprises an annular friction pad 152 having an outside diameter approximately equal to that of the open end 153 of turbine body 124 and an inner diameter to engage the outer surface of inflow conduit 130 in order to enclose the open end and prevent fluid passage therefrom. Pad 152 is biased distally, against the open end 153 of turbine body 124 by a spring 154 situated between pad 152 and the distal end of exhaust manifold 156 which surrounds inflow conduit 130. It will be understood that once a minimum amount of fluid pressure is built up within fluid conduit 130 and, therefore, within the interior chamber of turbine body 124, brake pad 152 will be pushed proximally (to the phantom position 156 shown) thereby allowing rotor 120 to rotate. Fluid will thereafter flow around pad 152 (providing pressure is maintained) and exit through exhaust manifold 156 as in the previously described embodiment.

An automatic centrifugal chuck device diagrammatically shown as device 160 may be used to secure a drill bit shaft 162 within the output shaft 122. Alternatively, a conventional manually adjustable chuck mechanism 164 may be used. In the preferred embodiment, the length L of the handpiece 100 may be on the order of 3.8 inches (96.5 mm) or so, depending upon the power desired from the turbine and the chuck mechanism used. Distal section 104 may vary considerably in length since its primary purpose is to serve as a handle as well as house the automatic chuck mechanism and bearings for the drive shaft. The diameter D1 may be 0.556 inches (14.12 mm) while diameter D2 could be on the order of 0.474 inches (12.04 mm).

Figure 5:
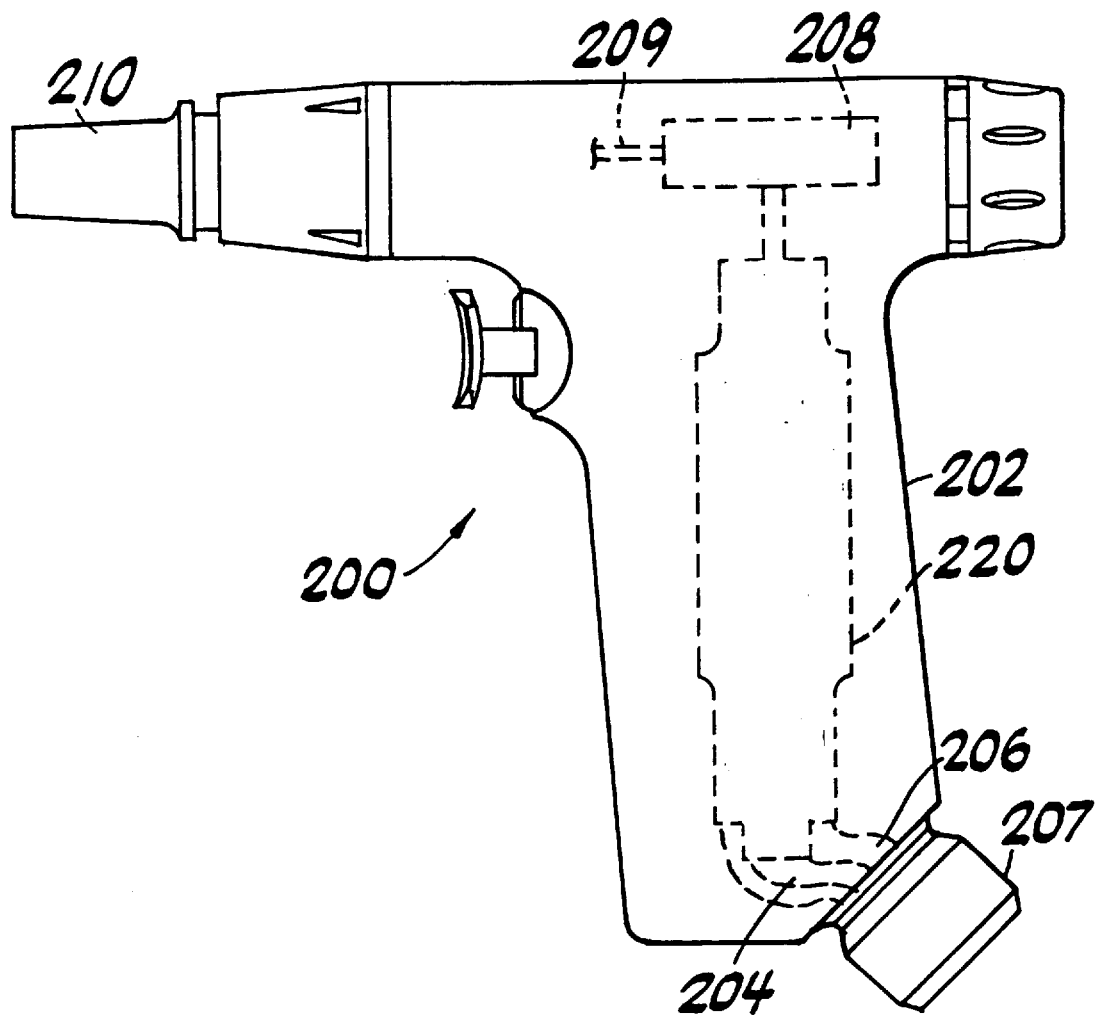
FIG. 5 is a diagrammatic view of a pistol-grip handpiece adapted to operate in accordance with the principles of this invention.

The embodiments of FIGS. 1, 2 and 3 show a tubular housing that also serves as the body of the handpiece to be directly held or gripped by a user. It will be understood that these embodiments could be adapted to other handpiece configurations in which a separate outer housing encloses the tubular housing 12 in a pistol-grip or other configuration. Thus, as shown in FIG. 5, the invention may be adapted to varying handpiece configurations such as, for example, pistol-grip handpiece 200. Handpiece 200 comprises a conventional rotary output handpiece body 202 (such as drill, wire driver, reamer, etc.) having concentric fluid inlet and outlet channels 204, 206 connected to a connector 207, a gear box 208 with a rotating output shaft 209 adapted to rotatingly drive a surgical instrument (not shown) secured to collet 210. A turbine assembly 220, essentially identical to the assembly of FIGS. 1 or 3, is enclosed within handpiece 200 in operative engagement with fluid inlet and outlet channels 204, 206 and gear box 208.

With various other modifications it will be understood that the handpieces powered by the turbine assemblies of FIGS. 1, 3 and 5 may be used to drive a surgical instrument in a reciprocating or oscillating manner.

Figure 8:
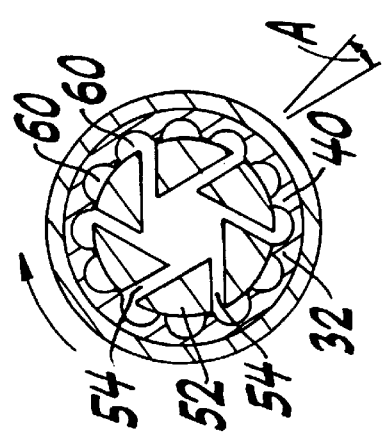
FIG. 8 is a sectional view of FIG. 6 taken along the line 8—8.
Figure 14:
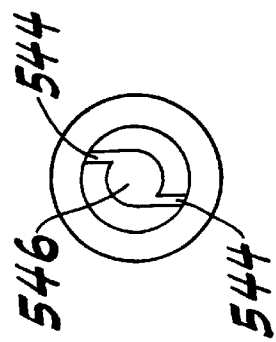
FIG. 14 is a sectional view of FIG. 11 taken along the line 14—14.
Figure 13:
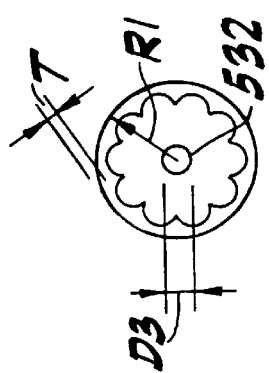
FIG. 13 is a sectional view of FIG. 11 taken along the line 13—13.
Figure 12:
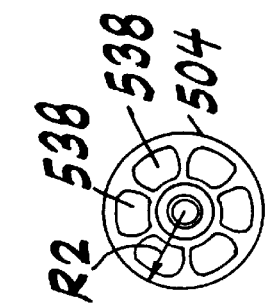
FIG. 12 is a sectional view of FIG. 11 taken along the line 12—12.

Another embodiment of a pencil-type handpiece is shown in FIGS. 6–8 operating on the same principles as the device is described above, with some changes. Handpiece 300 comprises a rotor 302 having hollow output shaft 304 provided with a bore 306 for receiving the shaft of an instrument or workpiece (not shown). The proximal end of bore 306 may communicate via bore 308 to the interior chamber of the rotor in order to provide an escape path for the fluid to prevent accidental turbine rotation if no instrument shaft is being driven. The interior surface of rotor 302 is provided with a plurality of longitudinal channels 310, each of the channels having a profile as best seen in FIG. 7 which allows the exhaust air coming from deflector cap 320 to impinge on the channels for a longer dwell time (as the rotor rotates) thereby increasing the efficiency of operation. Deflector cap 320 is provided with a diametrically opposed pair of tangentially directed, circular exhaust ports 322 and 324. For a given fluid pressure, the circular ports produce a higher velocity fluid stream than the elongated slots of other embodiments. Reducing the number of ports to two also increases the velocity and reduces manufacturing complexity. The open end of rotor 302 is enclosed by a brakepad 330 biased distally by a spring 332 compressed between the distal end 334 of exhaust manifold 336 and the distal side of brakepad 330. As shown in FIG. 8, brakepad 330 has a hexagonally profiled aperture 340 in order to keep it from rotating while enabling it to slide along a hexagonally profiled boss 342 formed around inlet channel 344. An annular recessed groove 350 is situated proximally of boss 342 in order to join annular chamber 352 with each of the annularly arranged exhaust channels 354.

Figure 9:
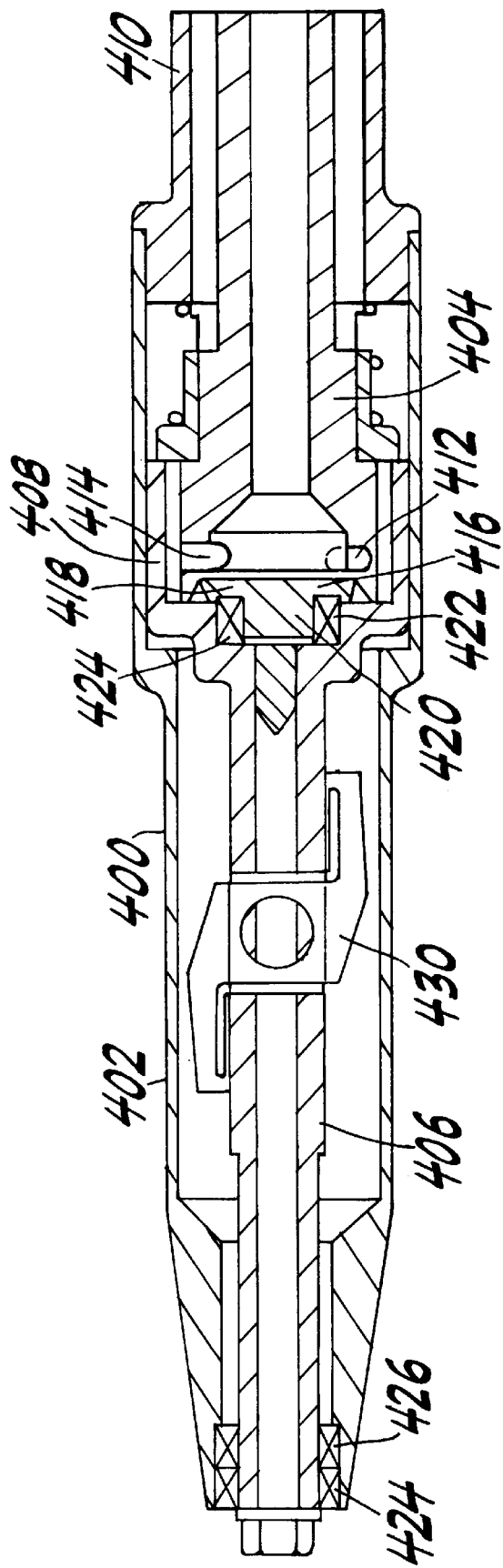
FIG. 9 is a schematic side elevational view in cross-section of another embodiment of a surgical handpiece constructed in accordance with the principles of this invention.
Figure 10:
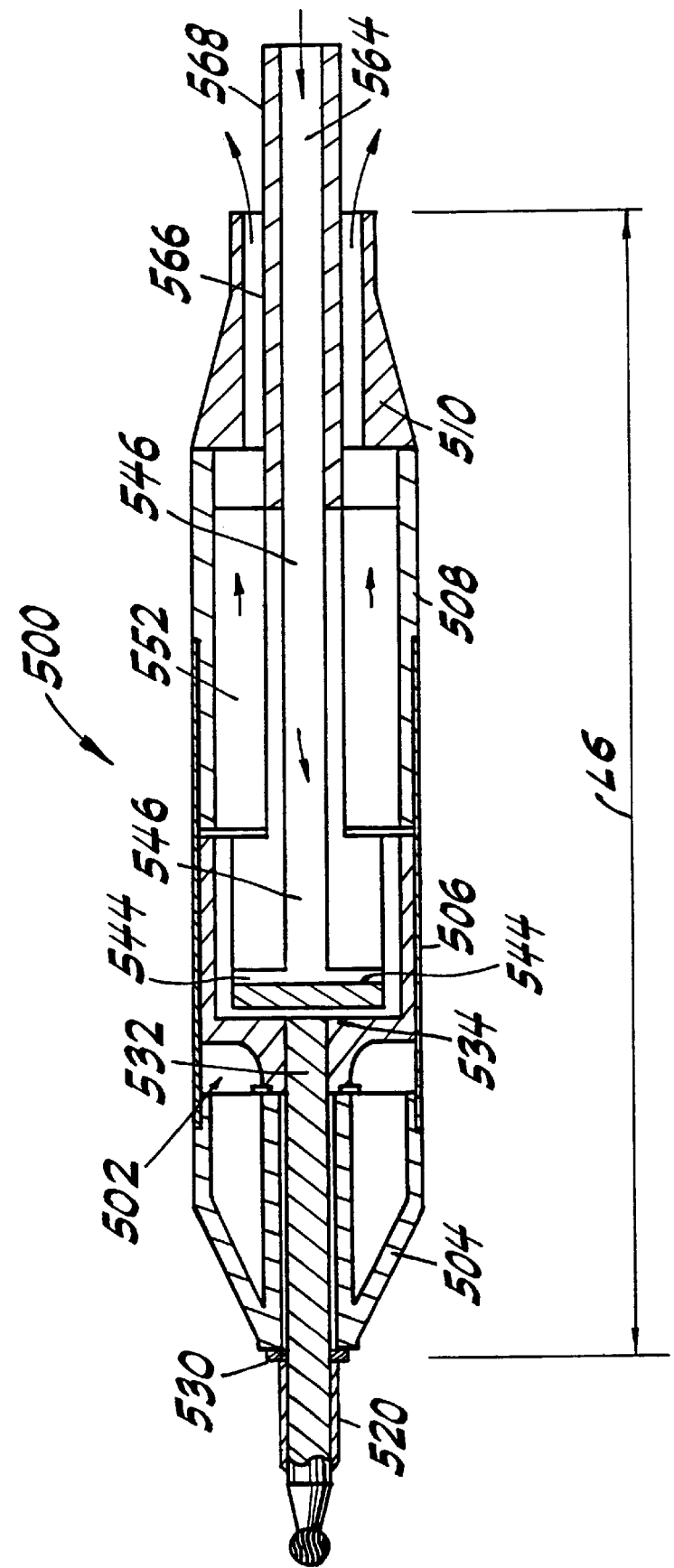
FIG. 10 is a side elevational view in cross-section of a disposable pneumatic motor/instrument assembly constructed in accordance with the principles of this invention.
Figure 11:
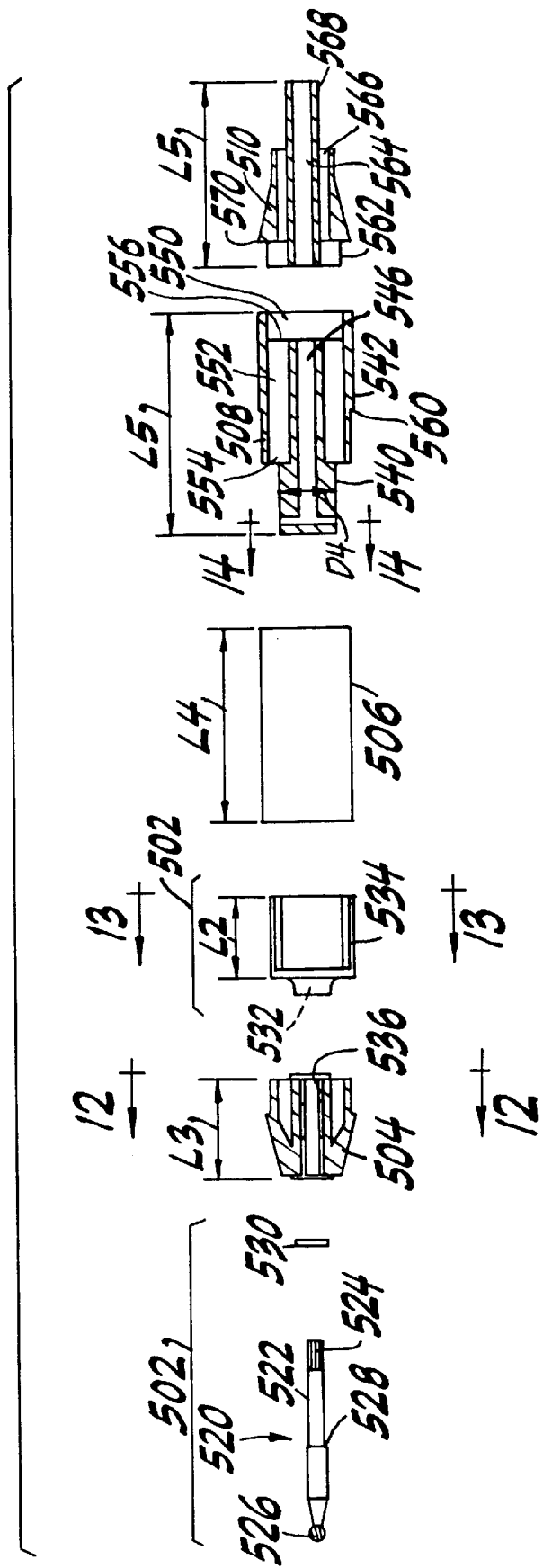
FIG. 11 is an exploded view of FIG. 10 showing some of the components in cross-section.

Another embodiment of the invention is shown in FIG. 9 in the form of handpiece 400 which operates on the same principles as the preceding embodiments. The primary distinction between handpiece 400 and the previous embodiments lies in the repositioning of the bearings supporting the output drive shaft. Thus, handpiece 400 comprises a housing 402 which includes a stationary deflector cap 404 and a rotating output shaft 406 attached to the distal end of rotatable turbine body 408. An exhaust manifold 410 is secured to the proximal end of deflector cap 404 and ideally is integrally formed therewith. Deflector 404 has two diametrically opposed tangential ports 412, 414 which operate analogously to previously described elements. The distal end of deflector cap 404 is joined to a transverse wall member 416 having a transverse wall portion 418 and an axially aligned bearing projection 420 on its distal side. Member 416 is welded or otherwise secured to the body of deflector cap 404 so that bearing projection 420 may be rotatably received within bearing 422 which is secured within a stepped-down shoulder portion 424 of the turbine body 408. Thus, it will be noted that drive shaft 406 is supported between proximal bearing 422 and distal bearings 424, 426 situated at the distal tip of the handpiece. The structure shown in this embodiment retains the cantilevered aspect of the turbine body while enabling any thrust load imposed upon drive shaft 406 to be absorbed by bearing 422 and the stationary elements proximal thereto. Centrifugal chuck 430, provided to automatically engage an instrument shaft inserted into the bore of hollow drive shaft 406, is the subject of a co-pending patent application Ser. No. 08/851,900, filed May 6, 1997 and assigned to the assignee hereof, which application is incorporated by reference herein. The remaining portions of this embodiment operate in a manner similar to that described above.

The various components of the handpieces disclosed herein may be made simply and inexpensively of plastic and/or inexpensive metal, ceramic or other non-metallic materials so that the entire device may be disposable. Alternatively, more robust and autoclavable or sterilizable components may be utilized if a reusable device is desired.

The simplicity of the entire assembly lends itself to a disposable pneumatic motor, especially if it is made entirely or partially of molded plastic, injection molded metal or a combination of both. As shown in FIGS. 10–14, a complete motor 500 comprises an instrument/turbine assembly 502, a distal nose/bearing assembly 504, a housing body 506, a stator body 508 and an inlet/exhaust body 510.

Instrument/turbine assembly 502 comprises an instrument such as a rotatable burr 520 having a shank 522 with a splined proximal end 524 and a distal burr head 526. Shank 522 is provided with a shoulder 528 against which a washer 530 rests in order to rotatably situate burr 520 within the distal nose/bearing assembly 504. The proximal splined end 524 of the burr shank is secured within bore 532 of cup-shaped rotor 534, the interior of which has a plurality of longitudinally extending channels similar to the rotor described above, as best seen in FIG. 13. The components of instrument/turbine assembly 502 may be made of various grades of plastic or stainless steel suitable for surgical instruments and rotor 534 may, if desired, be made from plastic or with a metal injection molding process to decrease the costs. If the rotor is molded from plastic, some auxiliary means for adding to the rotating mass (to increase momentum) may be necessary. For example, peripheral weighted pieces could be forced into or attached onto a plastic rotor. In the preferred embodiment, the length L2 may be on the order of 0.7 inches (17.78 mm), radius R1 may be on the order of 0.35 inches (8.89 mm), thickness T may be on the order of 0.072 inches (1.83 mm) and the diameter D3 of bore 532 may be on the order of 0.062 inches (1.57 mm).

Instrument/turbine assembly 502 is rotatably received within nose 504 which in the preferred embodiment has a length L3 on the order of 0.857 inches (21.76 mm) and a radius R2 on the order of 0.375 inches (9.52 mm). Burr 520 is rotatably received within bore 536 which is surrounded by a plurality of annularly arranged recesses 538. The distal nose/bearing assembly 504 may be made of a molded plastic material of suitable strength and rigidity with recesses 538 being provided to minimize the weight of the component. The proximal end of nose 504 is then abuttingly secured to the distal end of housing body 506 which surrounds rotor 534 and enables it to rotate within the housing 506. In the preferred embodiment, housing 506 may be made of thin walled stainless steel tube having a length L4 on the order of 1.662 inches (42.21 mm) and a diameter sufficient to be smoothly joined to nose 504.

Stator body 508 is provided with a distal deflector section 540 and a proximal support section 542. Deflector section 504 has a pair of laterally directed ports 544 extending outwardly from a central axially aligned channel 546, best seen in FIG. 14. Channel 546 extends into support section 542 and opens into a recess 550 formed at the proximal end of stator body 508. An annular exhaust channel 552 surrounds inflow channel 546 and extends through section 542 from its distal end 554 to its proximal end 556. As in the previously described embodiments, the exhaust from rotor 534 is received at end 554 and directed proximally. In the preferred embodiment, stator body 508 may be molded of a suitable plastic material having a length L5 on the order of 1.886 inches (47.90 mm) with the diameter D4 of the deflector section being on the order of 0.47 inches (11.93 mm). The diameter of the section 542 should be sufficient to accommodate the diameter of housing 506 which abuts against section 542 at annular ledge 560.

Recess 550 in the stator body receives distal projection 562 of inlet/exhaust body 510. Body 510 has an axially aligned throughbore 564 which serves as a continuation of inlet channel 546 and is provided with a plurality of annularly arranged exhaust channels 566 which receive exhaust fluid from exhaust channel 552 of the stator body. The proximal end of the inlet/exhaust body 510 may be provided with a short extension 568 in order to facilitate the connection of the body 510 to a coaxial inlet/exhaust tube (not shown). In the preferred embodiment, inlet/exhaust body 510 may be made of a suitable molded plastic material having a length L5 on the order of 1.57 inches (39.87 mm) and a maximum diameter at shoulder 570 sufficient to smoothly join the body 510 to body 508.

The overall length L6 of motor 500 may thus be on the order of 3.88 inches (98.55 mm) with a diameter on the order of 0.75 inches (19.05 mm). It will be noted, however, that various lengths and diameters may be produced depending upon the torque and speed requirements. Furthermore, the instrument may be a rotatable shaver blade rather than rotatable burr 520.

Figure 15:
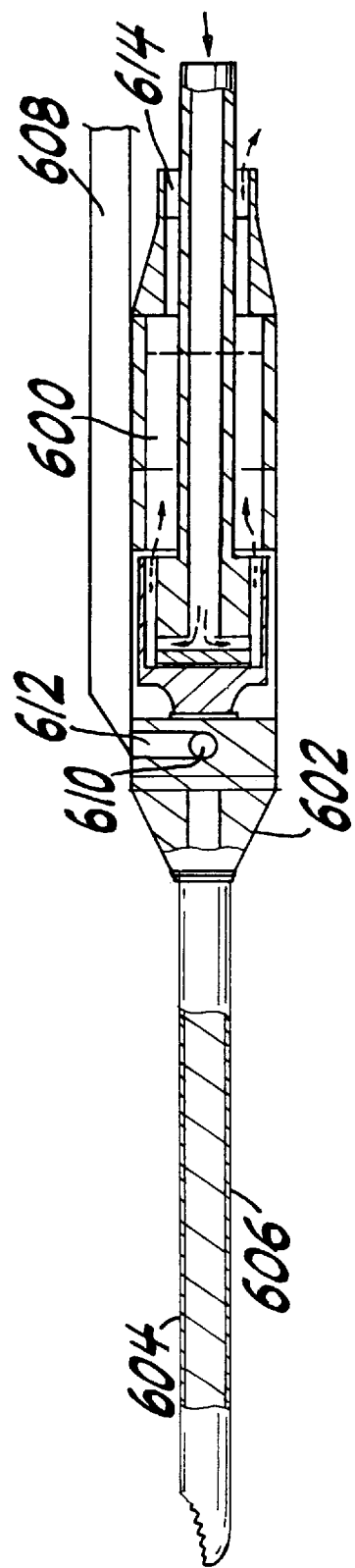
FIG. 15 is a side elevational view in cross-section of an alternate embodiment of a disposable pneumatic motor/instrument assembly constructed in accordance with the principles of this invention.

Rotatable shaver blades, as well as rotatable burrs, are commonly used in closed surgical procedures such as arthroscopic or, generally, endoscopic procedures. An example of such a shaver is shown in U.S. Pat. Nos. 5,269,798 (Winkler) and 5,269,794 (Rexroth), both assigned to the assignee hereof (or its affiliates), and incorporated by reference herein. A rotatable shaver comprises an elongated, tubular inner member having a cutting tip at its distal end and rotatably received within an elongated tubular outer member having a cutting window at its distal end. Any of the embodiments of the invention disclosed herein may be easily adapted to accept such an instrument as shown in FIG. 15. Thus, disposable instrument/turbine assembly 600 has a body 602 similar to that shown in FIGS. 10–14. The front end of the handpiece is adapted to receive a shaver blade 603 having an elongated stationary outer member 604 and an elongated, rotatable inner member 606. A separate vacuum or aspiration channel 608 may be provided to aspirate material through the lumen of the inner member via an aperture 610 at its proximal end and a communicating channel 612 (as best seen by reference to the aforementioned prior art patents). Vacuum in line 608 may be provided by a separate vacuum source or may be taken from the low pressure in exhaust channel 614.

It will be understood by those skilled in the art that numerous improvements and modifications may be made to the preferred embodiment of the invention disclosed herein without departing from the spirit and scope thereof.

What is claimed is:

1. A pneumatic surgical handpiece for driving a surgical instrument comprising:

a tubular housing having proximal and distal ends and an axis;

a rotor means for converting forces within a pressurized fluid to motion of the surgical instrument, said rotor means rotatably secured to said housing and comprising an axially aligned turbine body and an axially aligned output shaft extending distally from said turbine body, said turbine body comprising a distal end wall adjacent said output shaft, an open proximal end and an imperforate, axially aligned cylindrical wall extending proximally from said distal end wall toward said open proximal end, said imperforate cylindrical wall surrounding an interior chamber bounded circumferentially by the interior surface of said imperforate cylindrical wall;

a fluid inflow conduit means attached to said tubular housing for communicating pressurized fluid to said interior surface of said turbine body to rotate said rotor about said axis; and means for securing a surgical instrument to said output shaft for motion therewith.

2. A pneumatic surgical handpiece according to claim 1 wherein said fluid inflow conduit means further comprises a fluid dispersing means for communicating and directing fluid to said interior surface of said turbine body, said fluid dispersing means having a proximal end and a distal end and axially aligned within said interior chamber of said turbine body adjacent said interior surface, said proximal end connected to said fluid inflow conduit means and said distal end comprising a dispersing section having a cylindrical wall situated adjacent said interior surface and a plurality of ports in said cylindrical wall, said plurality of ports aligned to direct fluid from said fluid inflow conduit means toward said interior surface of said turbine body.

3. A pneumatic surgical handpiece according to claim 2 wherein said ports of said fluid dispersing means further comprise longitudinally extending slots obliquely extending through said cylindrical wall of said fluid dispersing means at a predetermined angle relative to said wall.

4. A pneumatic surgical handpiece according to claim 1 further comprising a plurality of channels circumferentially arranged and longitudinally extending along said interior surface, said channels open to said interior chamber of said turbine body and having a closed distal end and an open proximal end for enabling fluid flow therefrom.

5. A pneumatic surgical handpiece according to claim 4 wherein said interior surface is cylindrical and wherein said channels have a substantially semi-circular cross-section in a plane perpendicular to said axis.

6. A pneumatic surgical handpiece according to claim 1 wherein said output shaft is rotatably supported in a bearing means and wherein said turbine body proximal to said output shaft is cantilevered therefrom.

7. A pneumatic surgical handpiece according to claim 1 further comprising an annular exhaust conduit means for receiving fluid from said open end of said turbine body, said exhaust conduit means concentrically situated about a predetermined portion of said fluid inflow conduit means.

8. A pneumatic surgical handpiece according to claim 1 further comprising an annular brake means for preventing the rotation of said rotor means below a predetermined pressure of said pressurized fluid.

9. A pneumatic surgical handpiece according to claim 8 wherein said annular brake means comprises:

an annular friction pad member adapted to sealingly engage said open end of said turbine body to prevent fluid flow therefrom; and a spring member adapted to urge said friction pad member against said open end of said tubular body with a predetermined amount of pressure greater than said predetermined pressure of said pressurized fluid, said spring member enabling said pad member to be disengaged from said open end to permit fluid flow therefrom at fluid pressures greater than said predetermined pressure of said pressurized fluid.

10. A pneumatic surgical handpiece according to claim 1 further comprising safety interlock means for preventing torque transfer from said rotor to said output shaft until a surgical instrument is attached thereto.

11. A pneumatic surgical handpiece according to claim 10 wherein said safety interlock means comprises:

an axial bore in said output shaft for receiving a predetermined portion of the surgical instrument, said bore having a distal end open to the ambient and a proximal end;

a bypass channel means for joining said interior chamber of said turbine body and said proximal end of said bore in fluid communication, said bypass channel enabling fluid communication between said interior of said turbine body and the ambient when said predetermined portion of said surgical instrument is not received in said bore to thereby prevent pressure accumulation in said interior chamber until said predetermined portion of the surgical instrument is inserted into said axial bore.

12. A pneumatic surgical handpiece for driving a surgical instrument comprising:

a tubular housing having proximal and distal ends and an axis;

a rotor means comprising:
      a transverse wall;
      an output shaft extending distally from said transverse wall; and
      a hollow turbine body; extending proximally from said transverse wall for converting forces within a pressurized fluid to motion of said output shaft, said turbine body comprising an imperforate, axially aligned cylindrical wall extending proximally from said output shaft;

axially aligned fluid directing means for directing pressurized fluid to the interior of said turbine body; and means for securing a surgical instrument to said output shaft for motion therewith.

13. A pneumatic surgical handpiece according to claim 12 further comprising bearing means interposed between said housing and said output shaft for supporting said turbine body in a cantilevered manner.

14. A pneumatic surgical handpiece according to claim 12 further comprising:

a transverse cap member secured in axial alignment to the distal end of said fluid directing member;

a bearing projection extending distally from said cap member; and bearing means situated on the proximal side of said transverse end wall for engaging said bearing projection.

15. A pneumatic surgical handpiece for driving a surgical instrument comprising:
- a tubular housing having proximal and distal ends and an axis;
- a rotor means comprising:
  - a transverse wall;
  - an output shaft extending distally from said transverse wall and integrally formed with said surgical instrument; and
  - a hollow turbine body extending proximally from said transverse wall for converting forces within a pressurized fluid to motion of said output shaft, said turbine body extending proximally from said output shaft;
- axially aligned fluid directing means for directing pressurized fluid to the interior of said turbine body; and
- means for securing a surgical instrument to said output shaft for motion therewith.

16. A method of fluidically driving a surgical instrument within a handpiece comprising the steps of:
- providing a tubular housing having proximal and distal ends and an axis;
- providing within said housing a rotor means comprising an axially aligned turbine body and an axially aligned output shaft extending distally from said turbine body, said turbine body comprising a transverse distal end wall adjacent said output shaft, an open proximal end and an imperforate, axially aligned cylindrical wall extending proximally from said distal end wall toward said open proximal end, said imperforate cylindrical wall surrounding an interior chamber bounded circumferentially by the interior surface of said imperforate cylindrical wall;
- securing a surgical instrument to said output shaft for motion therewith; and
- directing pressurized fluid transversely to said interior surface of said turbine body, at a predetermined angle relative a radial line of said turbine body, to rotate said rotor means about said axis.

17. A method according to claim 16 further comprising the step of:
- rotatably supporting said rotor means in a cantilevered manner in one or more bearings adjacent said output shaft.

18. A method according to claim 16 further comprising the step of:
- directing said pressurized fluid axially in a distal direction prior to directing it transversely.

19. A method according to claim 16 further comprising the step of:
- directing said pressurized fluid proximally after it has contacted said interior surface of said turbine body.

20. A method according to claim 16 further comprising the step of:
- enabling said tubular housing to be directly held by a user.

21. A method according to claim 16 wherein said surgical instrument is integrally formed with said output shaft.

22. A method according to claim 21 wherein said surgical instrument further comprises a rotatable shaver blade and the method further comprises the steps of:
- non-rotatably axially securing an elongated outer member to the distal end of said housing;
- non-removably securing an elongated inner member to said output shaft.

* * * * *